July 24, 1973 H. C. BROWNELL Plant Pat. 3,374
ROSE PLANT
Filed Dec. 15, 1971
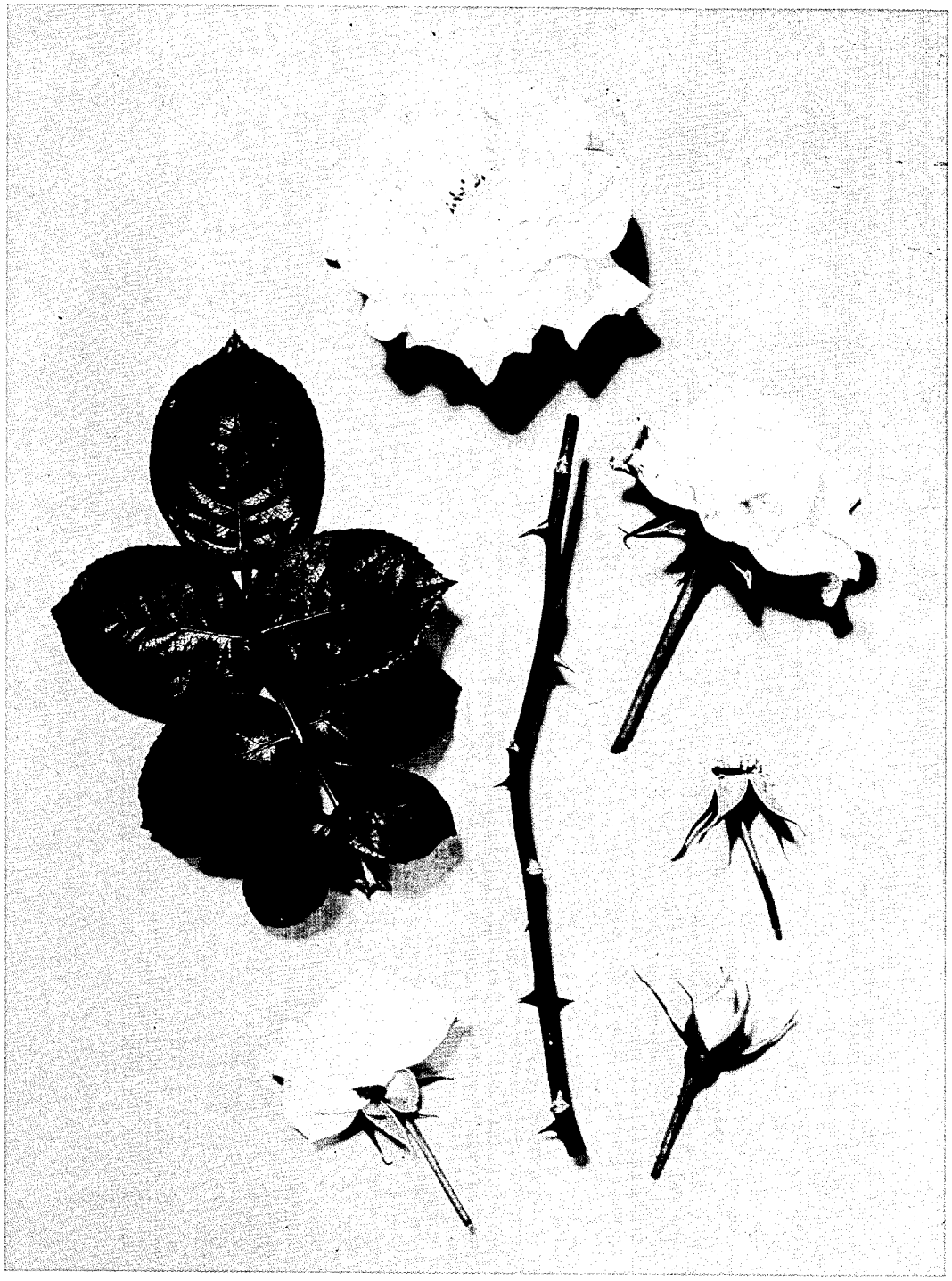
Inventor
Herbert C. Brownell United States Patent Office Plant Pat. 3,374
Patented July 24, 1973

3,374
ROSE PLANT

Herbert C. Brownell, Little Compton, R.I. 02837

Filed Dec. 15, 1971, Ser. No. 208,484
Int. Cl. A01h 5/00
U.S. Cl. Plt.—11 1 Claim My invention relates to roses and especially to a new, original and distinct variety of the class known commercially as "hybrid tea" and is a variant in that class, being a *Rosa wichuraiana* hybrid tea hybrid, produced by me and under my direction in the breeding grounds of my research gardens in Little Compton, Rhode Island, by selection of variety variations and by cross pollination, which can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the northern United States.

The light yellow (ordinary dictionary definition) of its petals combined with its characteristic of the outer ⅓ of the petals turning to a deep pink as it opens in combination with the unique brilliance thereof and their tendency to hold these colors under exposure, fading only very slightly under direct rays of the sun.

The novelty and variation within certain definite limits of the form of the bloom, the recurl of the petals as the flower opens, its character of holding its form for a long time and the petalage of the flowers;

Its unusual abundance of flowers, at bloom time and after early bloom time until frost;

Its character of ascending in height by recurrent branching and progressively longer stems from the base;

The character of producing many seven leafleted leaves, which character seldom has obtained on hybrid teas not having *Rosa wichuraiana* ancestry.

The accompanying drawings show typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flowers and garden decoration.
Class: Hybrid tea.
Breeding: Seedling.
*Seed parent.*—A known but unnamed seedling.
*Pollen parent.*—Peace—Plant Pat. No. 932.
Propagation: Holds its distinguishing characteristics through succeeding propagations by budding.

*Flower*

Locality where grown and observed: Little Compton, R.I., U.S.A.
Flowers borne: Singly and in clusters on stems of medium length and normal strength.
Quantity of bloom: Abundant, outdoors.
Continuity: Continuous during growing season until frost.
Fragrance: Moderate.

Bud:
*Peduncle.*—Average length and caliper; very few red hairs. Color—Pod Green, 061/1.
*Before calyx breaks.*—Size—medium. Form—globular; with slender foliaceous parts extending beyond the tip of the bud. Color—Lettuce green 861.
*As first petal opens.*—Size—medium. Form—globular. Color: Outside—Lettuce green 861. Inside—Pod green 061/2.
*Opening.*—Opens up well.
Bloom:
*Size (when fully open).*—Large; about 5 inches in diameter.
*Petalage.*—Double; from 45 to 50 petals; arranged regularly.
*Form.*—Globular, becoming cupped. Petals recurl slightly as bloom opens.
Petals:
*Texture.*—Thick; not satiny.
*Shape.*—Orbiculate, occasional notches.

This description of a newly opened flower was made from a rose grown outdoors at Little Compton, R.I. in the month of September.

*Color.*—Outer petal: outside and inside surface—Primrose Yellow 601/3. Inner petal: Outside surface—Primrose Yellow 601/3; inside surface—the top ¼ of petal Camellia Rose 622/3; balance of petal Primrose Yellow 601/1.
*Flower longevity.*—On bush in garden 5 or 6 days in September. Cut roses grown outdoors and kept at living room temperature 3 or 4 days in September.

*Reproductive organs*

Stamens: Numerous; arranged very irregular; all with anthers.
Filaments: Numerous; varying greatly in length; average caliper. Color—Orange 12.
Anthers: Numerous; all of which contain pollen. Color—Empire Yellow 603.
Pistils: Many.
Styles: Uneven; moderate length; average caliper. Color—Primrose Yellow 601/3.
Stigma: Color—Sulphur yellow 1/2.
Ovaries: Usually all enclosed in calyx.
Hips: Large; round; smooth. Color (mature)—Pod Green 061/1; darkening in part to Chrysanthemum Red 824/1.
Sepals: No sepals in plants observed.
Seeds: Medium to large; about 20 per hip.

*Plant*

Foliage:
*Leaves.*—Compound of usually 3 to 7 leaflets; normal quantity; medium to exceptionally large in size. Occasionally 2½ inches wide by 3 inches in length.
*Leaflets.*—Shape—ovate; pointed apex. Base—round. Margin—simply serrate.
*Color.*—Mature: Upper surface—Parsley green 00962; under surface—Sage green 000861/1.
*Rachis.*—Very short to medium in length. Upper side—grooved; smooth edges. Under side—smooth.
*Stipules.*—Short to medium; average width; with points from short to medium length, the upper of which normally form an angle of about 90 degrees.

*Disease resistance.*—About average with other varieties grown under comparable conditions at Little Compton, R.I.

Growth:

*Habit.*—Bushy; upright-spreading; much-branched; very tall; will grow to a height of six or seven feet if left untrimmed.

*Growth.*—Very vigorous.

*Canes.*—Average caliper.

*Main stems.*—Color—Fern green 0862/1 overlaid with Currant Red 821/1. Prickles—very few; average length; slightly hooked downward. Color—Erythrite Red 0027.

*Branches.*—Color—Fern green 0862/1. Prickles—same as main stems.

I claim:

1. A new and distinct variety of rose plant of the hybrid tea type, substantially as herein shown and described, characterized particularly as to novelty by its vigorous habit of growth, abundant foliage, and its ability to withstand moderate sub-zero temperatures in combination with its hybrid tea character and its *Rosa wichuraiana* ancestry.

No references cited.

ROBERT E. BAGWILL, Primary Examiner